United States Patent
Smart et al.

(10) Patent No.: US 8,642,744 B2
(45) Date of Patent: Feb. 4, 2014

(54) CROSSLINKING REAGENT FOR ANALYSIS OF PROTEIN-PROTEIN INTERACTION

(75) Inventors: Brian Phillip Smart, Cupertino, CA (US); James Alexander Apffel, Jr., Mountain View, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 503 days.

(21) Appl. No.: 12/914,800

(22) Filed: Oct. 28, 2010

(65) Prior Publication Data

US 2012/0107855 A1    May 3, 2012

(51) Int. Cl.
| | | |
|---|---|---|
| C07K 1/00 | (2006.01) |
| C07K 17/00 | (2006.01) |
| C07K 17/06 | (2006.01) |
| C12Q 1/00 | (2006.01) |
| C12N 11/00 | (2006.01) |
| C12N 11/06 | (2006.01) |

(52) U.S. Cl.
USPC ............... 530/402; 435/4; 435/174; 435/181; 530/810; 530/816

(58) Field of Classification Search
None
See application file for complete search history.

(56) References Cited

U.S. PATENT DOCUMENTS

| | | | | |
|---|---|---|---|---|
| 4,638,032 A | * | 1/1987 | Benner ...................... 525/54.11 |
| 5,399,671 A | * | 3/1995 | Kluger et al. ................. 530/385 |
| 5,656,720 A | * | 8/1997 | Schlueter et al. ............... 528/60 |
| 6,027,890 A | * | 2/2000 | Ness et al. ......................... 506/9 |
| 6,492,560 B2 | * | 12/2002 | Wilbur et al. .................. 564/505 |
| 7,094,413 B2 | * | 8/2006 | Buelow et al. ............. 424/278.1 |
| 8,124,364 B2 | * | 2/2012 | Sandberg et al. .............. 435/7.5 |
| 2006/0094121 A1 | | 5/2006 | Reid et al. |
| 2006/0115871 A1 | | 6/2006 | Bruce et al. |
| 2009/0053817 A1 | | 2/2009 | Reid et al. |

OTHER PUBLICATIONS

Amunugama et al., "Mechanisms for the Selective Gas-Phase Fragmentation Reactions of Methionine Side Chain Fixed Charge Sulfonium Ion Containing Peptides," Journal of the American Society for Mass Spectrometry, vol. 17, Issue 12, Dec. 2006, p. 1631-1642.
Leitner et al., "Probing Native Protein Structures by Chemical Cross-linking, Mass Spectrometry, and Bioinformatics," Mol. Cell Proteomics, 2010, 9(8), p. 1634-1649.
Rinner et al., "Identification of Cross-linked Peptides from Large Sequence Databases," Nat. Methods, 2008, 5(4), p. 315-8.
Zhang et al., "Identification of Protein-Protein Interactions and Topologies in Living Cells with Chemical Cross-linking and Mass Spectrometry," Mol. Cell Proteomics, 2009, 8(3), p. 409-20.

* cited by examiner

*Primary Examiner* — David M Naff

(57) ABSTRACT

Crosslinking reagents and methods for using the same for analysis of protein-protein interactions, are provided. The crosslinking reagents include a trifunctional scaffold that links two protein linking groups to each other and branches to link an affinity tag, where the protein linking groups can be fragmented from the scaffold. The distance between the two protein linking groups can be selected to crosslink two proteins of a protein complex via accessible amino acid residues. Also provided are crosslinked polypeptide compounds and kits that include crosslinking reagents. These reagents and methods find use in a variety of applications in which crosslinking of proteins in desired.

14 Claims, 3 Drawing Sheets ically, this setting is >100V; b) the fragmentor voltage is high enough to ensure efficient fragmentation of the crosslinker fragmentable linkage. This energy may be optimized by specific chemical design but in some cases is in the range of 100-300V; c) the fragmentor voltage is low enough to ensure little or no significant fragmentation of the backbone bonds or side chain bonds in the crosslinked peptides. In some cases, this energy may be <300V.

CROSSLINKING REAGENT FOR ANALYSIS OF PROTEIN-PROTEIN INTERACTION

INTRODUCTION

Many biological processes are mediated by non-covalently associated complexes of proteins. With advances in genome sequencing and proteomics, interest has grown in identifying proteins that are involved in cellular processes, and mapping networks of protein-protein interactions. Mass spectrometry has emerged as one technique in proteomics research for identifying proteins of interest, e.g., via sequencing of peptides in digests of the proteins.

Identifying and characterizing protein-protein interactions involved in biological processes are of great interest to researchers.

SUMMARY

Crosslinking reagents and methods for using the same for analysis of protein-protein interactions, are provided. The crosslinking reagents include a trifunctional scaffold that links to two protein linking groups and also links to an affinity tag. The protein linking groups can be fragmented from the scaffold. Also provided are crosslinked polypeptide compounds and kits that include crosslinking reagents. These reagents and methods find use in a variety of applications in which crosslinking of proteins is desired.

DEFINITIONS

Figure 1:
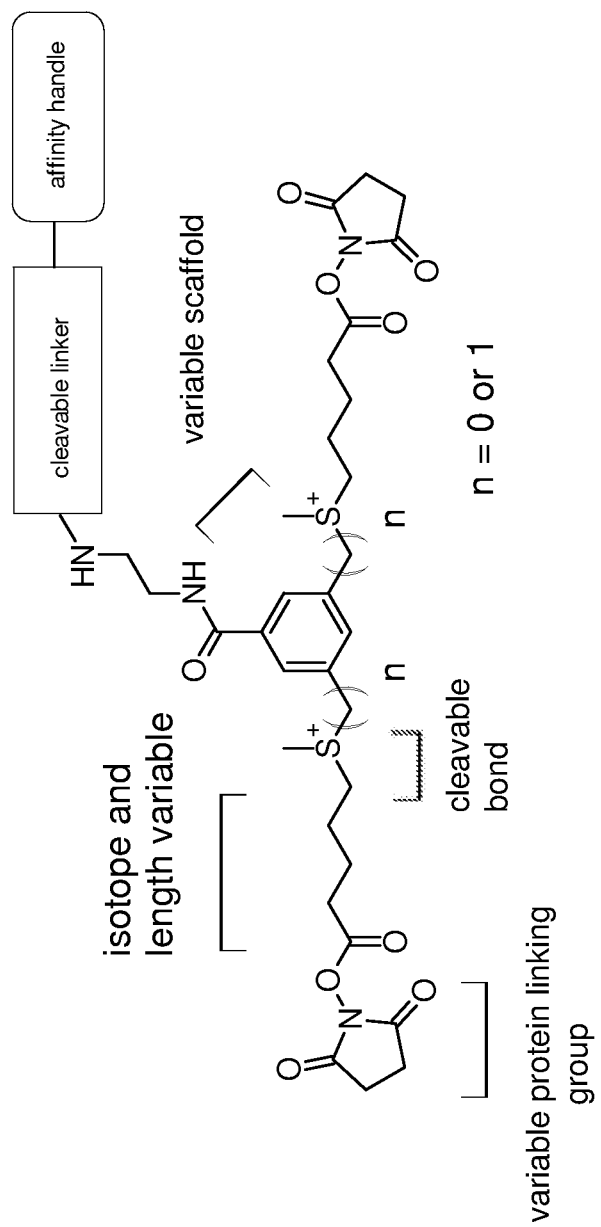
FIG. 1 illustrates an exemplary crosslinking reagent.
Figure 2:
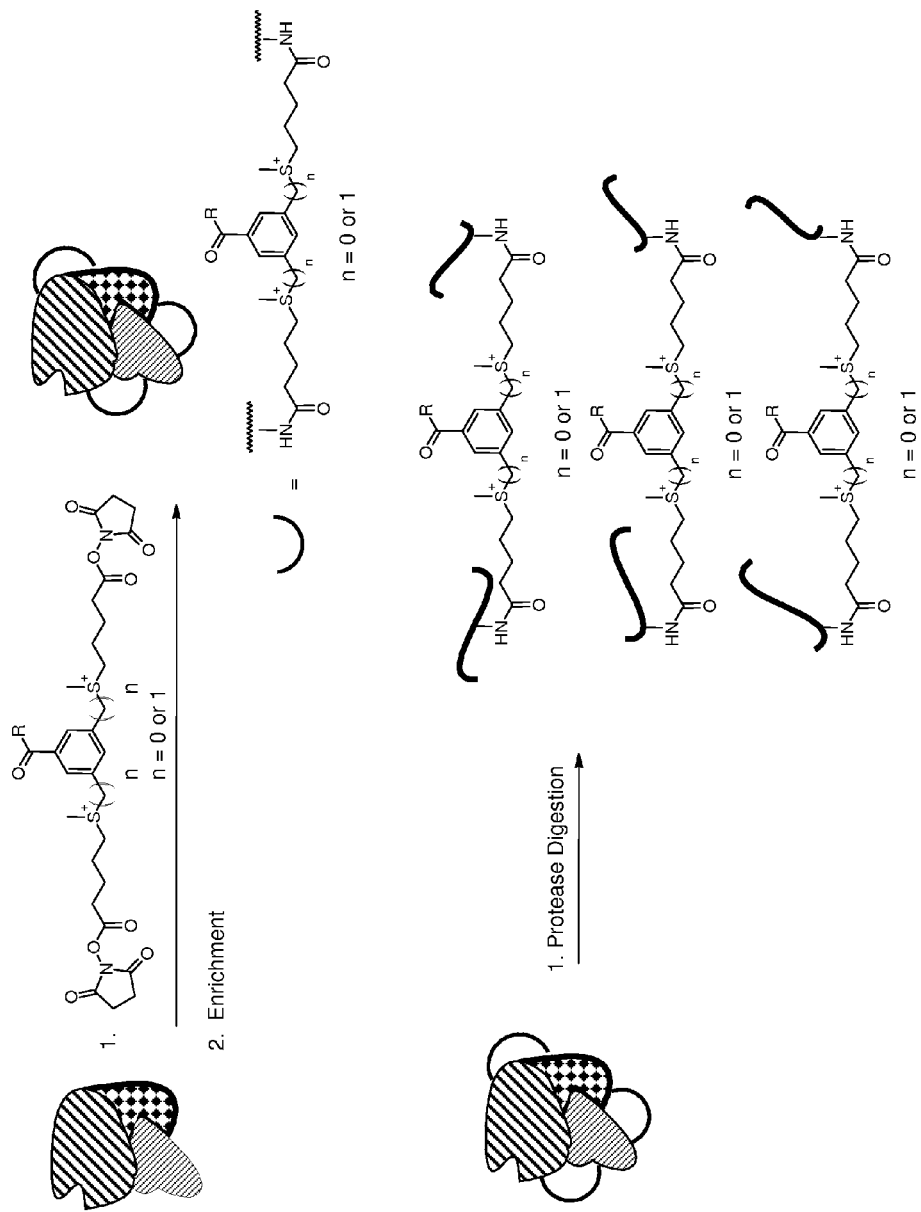
FIG. 2 depicts an exemplary method of crosslinking the proteins of a protein complex using a subject crosslinking reagent, followed by protease digestion to produce crosslinked peptides.

Unless defined otherwise, all technical and scientific terms used herein have the same meaning as commonly understood by one of ordinary skill in the art to which this invention belongs. Still, certain terms are defined below for the sake of clarity and ease of reference.

As used herein, the terms "polypeptide" and "protein" are used interchangeably. The term "polypeptide" also includes post translational modified polypeptides or proteins. The term "polypeptide" includes polypeptides in which the conventional backbone has been replaced with non-naturally occurring or synthetic backbones, and peptides in which one or more of the conventional amino acids have been replaced with one or more non-naturally occurring or synthetic amino acids. In general, polypeptides may be of any length, e.g., greater than 2 amino acids, greater than 4 amino acids, greater than about 10 amino acids, greater than about 20 amino acids, greater than about 50 amino acids, greater than about 100 amino acids, greater than about 300 amino acids, usually up to about 500 or 1000 or more amino acids. "Peptides" are generally greater than 2 amino acids, greater than 4 amino acids, greater than about 10 amino acids, greater than about 20 amino acids, usually up to about 9, 10, 20, 30 or 50 amino acids. In some embodiments, peptides are between 5 and 30 amino acids in length. A peptide may be made by protease digestion of a large polypeptide.

As used herein, the term "fragmentable" in the context of "fragmentable bond" refers to a covalent bond in a molecule that can be selectively fragmented to produce two products. Application of a suitable fragmentation stimulus to a molecule that contains more than one fragmentable bond that are fragmented by the stimulus will produce more than two products.

As used herein, the term "fragmentation conditions" refers to the conditions by which a fragmentable bond may be selectively fragmented. Ionization conditions that do not fragment the backbone of a peptide are an example of a fragmentation condition.

As used herein, the term "heterosubstituted carbonyl group" refers to a carbonyl group —C(=O)— in which the carbonyl oxygen is replaced by another heteroatom having at least one lone pair of electrons. Examples of heterosubstituted carbonyl groups include the group —C(=Y)—, where Y is S or NR$^3$ and R$^3$ is selected from hydrogen and an alkyl. A compound that is otherwise identical to the unfragmented compound of FIG. 3 except that it contains heterosubstituted carbonyl groups instead of carbonyl groups adjacent to peptides 1 and 2 is capable of undergoing the reaction shown in FIG. 3. This reaction occurs via a nucleophilic substitution reaction of the heteroatoms containing at least one lone pair of electrons with atoms that are adjacent to the sulphonium, phosphonium or ammonium leaving groups to break the covalent bonds adjacent to the sulphonium, phosphonium or ammonium leaving groups, releasing a reporter product and two peptide-containing products that are each positively charged.

As used herein, the term "ionization conditions that do not fragment the backbone of a peptide" and grammatical equivalents thereof refers to ionization conditions, in a mass spectrometer system, that have an energy that is insufficient to significantly cleave any of the bonds in the peptide backbone of [Glu1]-fibrinopeptide B. One example of such conditions are the conditions inside the ion source of an Agilent 6530 series QTOF mass spectrometer, operating under standard parameters for peptide analysis, in which a so-called "in-source" potential of 250 Volts is applied. In this specific instrument, the "fragmentor" voltage may be optimized to meet the following criteria: a) the fragmentor voltage is high enough to ensure high transmission of ions exiting the transfer capillary and entering the first skimmer. Typically this setting is >100V; b) the fragmentor voltage is high enough to ensure efficient fragmentation of the crosslinker fragmentable linkage. This energy may be optimized by specific chemical design but in some cases is in the range of 100-300V; c) the fragmentor voltage is low enough to ensure little or no significant fragmentation of the backbone bonds or side chain bonds in the crosslinked peptides. In some cases, this energy may be <300V.

As will be described in greater detail below, the energy required to provide such conditions may vary greatly depending on the manufacturer and design of the mass spectrometer system used. Such conditions may also be produced in other parts of a mass spectrometry system, e.g., in a collision cell.

Certain embodiments described in this disclosure may refer to a bond or linkage that is fragmentable in a mass spectrometer system under ionization conditions that do not fragment the backbone of the crosslinked peptides. In these embodiments, the fragmentable bond is fragmented at an energy that is insufficient to significantly fragment any of the bonds in the peptide backbone of [Glu1]-fibrinopeptide B. An example of such conditions is described above. An example of such a fragmentable bond is the bond that is present between a sulphonium group (that is linked to the scaffold) and its adjacent carbon in the methylene group that is part of the linker between the scaffold and a crosslinked compound of the claimed invention, i.e., the —CH$_2$—S$^+$(CH$_3$)— fragmentable bond depicted in FIG. 1.

As used herein, the term "reporter product" refers to the product that contains the trifunctional scaffold component of the crosslinking reagent and that is produced after fragmentation of the fragmentable bonds of a subject crosslinked compound. An example of such a reporter product is the "reporter ion" depicted in FIG. 3. The reporter product has a characteristic m/z value when analyzed by mass spectroscopy.

As used herein, the term "trifunctional scaffold" refers to a moiety that connects three linkages to three distinct linked groups. A trifunctional scaffold may be a single atom or a group containing 30 carbons or less. Exemplary trifunctional scaffolds include: 1) an aryl group (e.g., a phenyl group) that includes three substituents that each connect to one of the linked groups; 2) a trisubstituted nitrogen atom; and 3) an amino acid where the amino group, the carboxylic acid group and the sidechain group of the amino acid each connect to one of the linked groups.

As used herein, the term "linker" or "linkage" refers to a linking moiety that connects two groups and has a backbone of 20 atoms or less in length. A linker or linkage may be a covalent bond that connects two groups or a chain of between 1 and 20 atoms in length, for example of about 1, 2, 3, 4, 5, 6, 8, 10, 12, 14, 16, 18 or 20 carbon atoms in length, where the linker may be linear, branched, cyclic or a single atom. In certain cases, one, two, three, four or five or more carbon atoms of a linker backbone may be optionally substituted with a sulfur, nitrogen or oxygen heteroatom. The bonds between backbone atoms may be saturated or unsaturated, usually not more than one, two, or three unsaturated bonds will be present in a linker backbone. The linker may include one or more substituent groups, for example with an alkyl, aryl or alkenyl group. A linker may include, without limitations, oligo(ethylene glycol); ethers, thioethers, tertiary amines, alkyls, which may be straight or branched, e.g., methyl, ethyl, n-propyl, 1-methylethyl (iso-propyl), n-butyl, n-pentyl, 1,1-dimethylethyl (t-butyl), and the like. The linker backbone may include a cyclic group, for example, an aryl, a heterocycle or a cycloalkyl group, where 2 or more atoms, e.g., 2, 3 or 4 atoms, of the cyclic group are included in the backbone. A linker may be cleavable or non-cleavable.

As used herein, the term "cleavable linker" refers to a linker that can be selectively cleaved to produce two products. Application of suitable cleavage conditions to a molecule containing a cleavable linker that is cleaved by the cleavage conditions will produce two byproducts. A cleavable linker of the present invention is stable, e.g. to physiological conditions, until it is contacted with a cleavage-inducing stimulus, e.g., an agent such as an enzyme or other cleavage-inducing agent such as chemical agent or light. Exemplary conditions are set forth below.

For clarity, the number of atoms that connect two groups is calculated by counting the minimum number of covalently linked atoms between the two groups, excluding atoms of the two groups themselves. When the linkage between two groups includes a cyclic moiety, the shortest path around the ring of the cyclic moiety is counted so that a minimum possible number of atoms that connect the two groups is calculated.

As used herein, the term "affinity tag" refers to a member of a specific binding pair, i.e. two molecules where one of the molecules through chemical or physical means specifically binds to the other molecule. The complementary member of the affinity tag may be immobilized (e.g., to a chromatography support, a bead or a planar surface) to produce an affinity chromatography support that specifically binds the affinity tag. Tagging a compound of interest with an affinity tag allows the compound to be separated from a mixture of untagged compounds by affinity, e.g., using affinity chromatography. Examples of specific binding pairs include biotin and streptavidin (or avidin), and antigen and antibody, although binding pairs, e.g., nucleic acid hybrids, polyhistidine and nickel, and azido and alkynyl (e.g., cyclooctynyl) or phosphino groups are also envisioned. The specific binding pairs may include analogs, derivatives and fragments of the original specific binding members.

As used herein, the term "biotin moiety" refers to an affinity tag that includes biotin or a biotin analogue such as desthiobiotin, oxybiotin, 2'-iminobiotin, diaminobiotin, biotin sulfoxide, biocytin, etc. Biotin moieties bind to streptavidin with an affinity of at least $10^{-8}$ M. A biotin moiety may also include a linker, e.g., -LC-biotin, -LC-LC-Biotin, -SLC-Biotin or -PEG$_n$-Biotin where n is 3-12 (commercially available from Pierce Biotechnology).

As used herein, the term "substituted" refers to a group in which one or more atoms of the group are each independently replaced with a substituent(s), where the atom being replaced may be a hydrogen or non-hydrogen atom (e.g., a carbon or a heteroatom). A group that is "substituted" can have 1 or more substituents, where the substitutents are independently selected from the group consisting of acyl, acylamino, acyloxy, alkoxy, alkoxycarbonyl, alkoxycarbonylamino, alkyl, trihaloalkyl, alkenyl, alkynyl, amino, amido, imino, aminocarbonyl, aminocarbonylamino, aminocarbonyloxy, aryl, aryloxy, azido, diazo, carboxyl, carbonyl, cyano, isocyanate, isothiocyanate, cycloalkyl, guanidyl, halogen, heterocyclyl, heterocyclyloxy, hydroxyl, keto, nitro, nitroso, oxo, thio, thioether, thioalkoxy, thioaryloxy, thioketo, thiol, sulfonate, sulfinate, phosphinate, phosphonate, alkyl-S(O)—, aryl-S(O)—, alkyl-S(O)$_2$— and aryl-S(O)$_2$.

As used herein, the term "protein linking group" refers to a group that is capable of reacting directly either spontaneously or after activation through contact with a stimulus, e.g., light, with an accessible sidechain functional group of a protein under aqueous conditions to produce a covalent linkage to the protein. The protein linking group is capable of reacting under aqueous conditions at which proteins of interest are able to be maintained in a folded state (e.g., physiological conditions). The protein linking group may react with the sidechain functional groups of a Lys, Cys, Ser, Thr, Tyr, His or Arg amino acid residue in a protein of interest to produce a covalent linkage to the protein. The protein linking group may also react with a terminal group of the protein, e.g., the amino terminus. Thus, the protein linking group may be amino-reactive, thiol-reactive, hydroxyl-reactive, imidazolyl-reactive or guanidinyl-reactive. Exemplary protein linking groups include active esters (e.g., an amino-reactive NHS ester), and thiol-reactive maleimide or iodoacetamide groups. Further exemplary protein linking groups and methods of using the same are described in Hermanson, "Bioconjugate Techniques" 2nd Edition, Academic Press, 2008.

As used herein, the term "to cross-link" refers to the process of linking two moieties or atoms to each other via a covalent bond. An exemplary cross-linking process is the reaction of a protein linking group with the sidechain residue of a protein of interest to produce a stable covalent linkage.

As used herein, the term "leaving group" refers to group that is capable of being displaced from an adjacent atom during a nucleophilic substitution reaction or a nucleophilic acyl substitution reaction at that adjacent atom. One exemplary leaving group is the N-hydroxysuccinimidyl groups (NHS) of the NHS ester protein linking groups depicted in FIG. 1, that are displaced from carbonyl groups of the crosslinking reagent during crosslinking. Other exemplary leaving groups are the sulfonium groups (—S⁺(Me)R) of the crosslinking reagent depicted in FIG. 1 that are disconnected from the adjacent carbon atoms during fragmentation of the fragmentable bonds to produce neutral thioether groups (S(Me)R).

The compounds of the invention may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as, their racemic and optically pure forms. Optically active (+) and (−), (R)- and (S)-, or (D)- and (L)-isomers may be prepared using chiral synthons or chiral reagents, or resolved using conventional techniques, such as reverse phase HPLC. When the compounds described herein contain olefinic double bonds or other centers of geometric asymmetry, and unless specified otherwise, it is intended that the compounds include both E and Z geometric isomers Likewise, all tautomeric forms are also intended to be included.

Before the present invention is described in greater detail, it is to be understood that this invention is not limited to particular embodiments described, and as such may, of course, vary. It is also to be understood that the terminology used herein is for the purpose of describing particular embodiments only, and is not intended to be limiting, since the scope of the present invention will be limited only by the appended claims.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Where a range of values is provided, it is understood that each intervening value, to the tenth of the unit of the lower limit unless the context clearly dictates otherwise, between the upper and lower limit of that range and any other stated or intervening value in that stated range is encompassed within the invention.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

The headings provided herein are not limitations of the various aspects or embodiments of the invention. Accordingly, the terms defined immediately below are more fully defined by reference to the specification as a whole.

DETAILED DESCRIPTION OF EXEMPLARY EMBODIMENTS

As noted above, crosslinking reagents and methods for using the same in the analysis of protein-protein interactions are provided. The subject crosslinking reagents contain a reporter component and two fragmentable bonds that can be selectively fragmented under ionization conditions that do not fragment the backbone of the crosslinked peptide. Analysis of the subject crosslinked peptides by mass spectroscopy is simplified when these fragmentable bonds are fragmented without fragmentation of the backbones of the peptides, because fragmentation of the crosslinked peptides releases two peptide products in conjunction with a characteristic reporter product that identifies the presence of the peptide products. The reporter product has a mass that is independent of the peptidic content of the crosslinked peptides and gives characteristic mass to charge ratios, i.e., m/z values. The peptide products produced after cleavage of the fragmentable bonds of the crosslinked peptides may be selected for further sequence analysis (e.g., by tandem mass spectroscopy) to determine the identity of parent proteins that were crosslinked and also specific regions of these proteins that were crosslinked.

The subject crosslinking reagents include a trifunctional scaffold that connects to two protein linking groups via fragmentable bonds and an affinity tag via an optionally cleavable linker. The subject crosslinking reagents may include one or more isostopically labeled atoms such that the subject crosslinked polypeptides produce fragmentation products (e.g., a reporter product and/or peptide-containing products) containing characteristic isotopic signatures, that facilitates the identification and further analysis of the fragmentation products.

Methods of analyzing protein-protein interactions are also provided. In general terms, proteins that are interacting in their native forms are crosslinked via the protein linking groups of a subject crosslinking reagent. Subsequent digestion of the crosslinked proteins using one or more proteases produces a mixture of digestion products containing both crosslinked and non-crosslinked peptides. Since the subject crosslinking reagent may include an optional affinity tag, any crosslinked peptides in the mixture may be optionally separated from non-crosslinked peptides using affinity chromatography prior to analysis. Fragmentation of the fragmentable bonds of the crosslinked peptides in the mass spectrometer system under conditions that do not fragment the backbone of a peptide produces first and second peptide products in conjunction with a characteristic reporter product. Sequence analysis of the first and second peptide products (e.g., using mass spectrometry) can then be performed to identify sequences that correspond to the crosslinking sites of the parent interacting proteins. Isotopic labels may be included at any convenient position in the crosslinking reagent to facilitate analysis of the peptide products.

The subject crosslinking reagents find use both in a cell free assay (e.g., using isolated proteins, cell lysates, isolated organelles, isolated membranes such as nuclear membrane, or any other fraction of a cell) and on intact cells (e.g., cells grown in culture). In some embodiments, the cell permeability of the crosslinking reagent is modulated such that the crosslinking reagent may target proteins of interest at specific sites within a cell. Crosslinking reagents of the invention provide for enrichment and/or isolation of crosslinked products from non-crosslinked material, e.g., via the binding of an affinity tag to a chromatographic support.

In order to further illustrate certain aspects of the present invention, the following specific examples are provided.

Crosslinking Reagents

In some embodiments, the crosslinking reagent is described by formula (I):

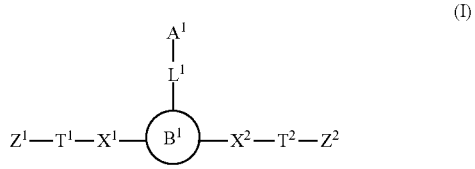

where $A^1$ is an affinity tag;
$L^1$ is a linker;
$T^1$ and $T^2$ are each independently a linker of 3 to 6 atoms (e.g., 3, 4, 5 or 6 atoms) in length;
$B^1$ is a trifunctional scaffold;
$X^1$ and $X^2$ are independently selected from a sulfonium group, a phosphonium group and an ammonium group; and
$Z^1$ and $Z^2$ each independently include a protein linking group;
where $Z^1$ and $Z^2$ each include a carbonyl or a heterosubstituted carbonyl group in a position adjacent to $T^1$ and $T^2$ respectively.

The affinity tag allows crosslinked polypeptide products to be separated from a mixture of untagged polypeptides by affinity, e.g., using affinity support, e.g., a chromatography column or magnetic beads. Examples of affinity capture components include, but are not limited to, a ligand and a receptor (e.g., biotin and avidin), an antibody and an antigen, complementary polynucleotides, an aptamer and a small molecule, a polyhistidine tag and nickel, and a reactive group such as a thiol, which can undergo a Michael addition with an electrophilic group, or form a disulfide bond with another thiol group. The specific binding pairs may include analogs, derivatives and fragments of the original specific binding members. For example, an antibody directed to a protein antigen may also recognize peptide fragments, chemically synthesized, labeled protein, derivatized protein, etc. so long as an epitope is present. In certain embodiments, the affinity tag includes biotin. Other affinity tags or reactive groups that may be used include, but are not limited to: polyhistidine (e.g., 4 to 14, such as 6 to 10 residues), benzophenone, a sulfhydryl group, an aryl azide and an azirine.

In particular embodiments, the affinity tag includes a biotin moiety, such as biotin, desthiobiotin, oxybiotin, 2'-iminobiotin, diaminobiotin, biotin sulfoxide, biocytin, etc. The biotin moiety is capable of specifically binding with high affinity to a support e.g., a chromatography support that contains immobilized avidin, neutravidin or streptavidin. In some cases, a monomeric avidin support may be used to specifically bind biotinylated crosslinked polypeptides with moderate affinity thereby allowing bound crosslinked polypeptides to be later eluted competitively (e.g., with a 2 mM biotin solution or using a highly organic elution solution, e.g., 70% acetonitrile) after non-biotinylated polypeptides have been washed away.

In some cases, the biotin moiety is connected to the crosslinking reagent via a linker (see e.g., linker $L^1$ depicted in formula (I) above). In other cases, the linker connected to the biotin moiety is a cleavable linker, e.g., a photocleavable linker, an enzymatically cleavable linker or a chemoselectively cleavable linker. A variety of cleavable and non-cleavable linkers are known to those of skill in the art and find use in the subject crosslinking reagents, e.g., as described in Olejnik et al. (Methods in Enzymology 1998 291:135-154), and further described in U.S. Pat. No. 6,027,890; Olejnik et al. (Proc. Natl. Acad Sci, 92:7590-94); Ogata et al. (Anal. Chem. 2002 74:4702-4708); Bai et al. (Nucl. Acids Res. 2004 32:535-541); Zhao et al. (Anal. Chem. 2002 74:4259-4268); and Sanford et al. (Chem. Mater. 1998 10:1510-20). Cleavable linkers that may be employed in the subject crosslinking reagents include electrophilically cleavable linkers, nucleophilically cleavable linkers, photocleavable linkers, metal cleavable linkers, electrolytically-cleavable, enzymatically cleavable linkers, and linkers that are cleavable under reductive and oxidative conditions. When the biotin moiety is connected to the crosslinking reagent via a cleavable linker, that linker may be selectively cleaved without breaking the fragmentable bonds in the molecule (i.e., the fragmentable bonds connecting the protein linking groups with the scaffold). Exemplary cleavable linkers useful for connecting to the affinity tag may include photo-sensitive groups comprising bonds that break upon exposure to light of a certain wavelength. Suitable photocleavable linkers for use in the subject crosslinking reagents include ortho-nitrobenzyl-based linkers, phenacyl linkers, alkoxybenzoin linkers, chromium arene complex linkers, NpSSMpact linkers and pivaloylglycol linkers, as described in Guillier et al. (Chem. Rev. 2000 1000: 2091-2157). For example, a 1-(2-nitrophenyl)ethyl-based photocleavable linker (Ambergen) can be efficiently cleaved using near-UV light, e.g., in >90% yield in 5-10 minutes using a 365 nm peak lamp at 1-5 mW/cm².

In certain embodiments, crosslinked polypeptides bound to an affinity support via an affinity tag can be removed from the support by cleavage of the cleavable linker that connects the affinity tag to the trifunctional scaffold, after washing the affinity support to remove any untagged polypeptides. For example, the cleavable linker may be photocleaved (e.g., using UV light) to release the crosslinked polypeptides for subsequent analysis by mass spectroscopy. See e.g., the "cleavable linker" of FIG. 1.

The trifunctional scaffold of the subject crosslinking reagents may be any suitable linking group that is capable of linking the affinity tag and the two protein linking groups. A variety of such scaffolds is known to those of skill in the art and finds use in the subject crosslinking reagents. The trifunctional scaffold may be a single atom (e.g., a trisubstituted nitrogen atom), an amino acid moiety (e.g., where the amino, carboxylic acid and sidechain groups of the amino acid each connect to one of the three linked groups), or an aryl or heteroaryl group (e.g., a phenyl or a pyridyl group) that includes three substituents each connecting to one of the three linked groups. The trifunctional scaffold may be a polycyclic aromatic or heteroaromatic group, such as a naphthalene, an anthracene or a quinoline. The trifunctional scaffold may be further substituted with one or more substituents that may confer on the resulting crosslinking reagent variant a desirable property such as increased solubility, or a particular stability. In certain embodiments, substitutents of the trifunctional scaffold are selected to modulate (e.g., via electronic or steric effects) the fragmentation of the adjacent fragmentable bonds in a mass spectrometer system under ionization conditions that do not fragment the backbone of peptides. Such substituents may modulate the stability of the fragmentable bonds to the ionization conditions such that the sensitivity of the analysis is optimized, e.g., the ionization efficiency of the crosslinked peptides is optimized under ionization conditions that break the fragmentable bonds but that do not fragment the backbones of the peptides.

In certain embodiments, the crosslinking reagent is described by formula (I), where the bond between $T^1$ and $X^1$ and the bond between $T^2$ and $X^2$ are each fragmentable in a mass spectrometer system under ionization conditions that do not fragment the backbone of a peptide.

Figure 3:
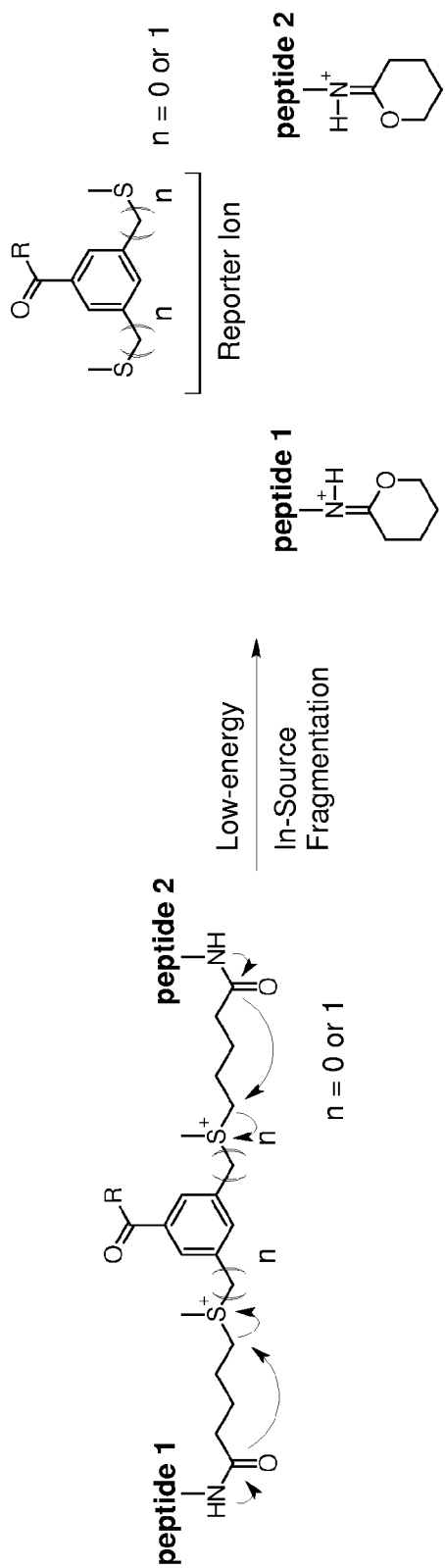
FIG. 3 illustrates certain principles of the subject method.

The subject crosslinking reagent includes two fragmentable bonds in the linking arms of the reagent that contain the protein linking groups. The fragmentable bonds each connect a leaving group (e.g., a sulfonium, phosphonium or ammonium leaving group) to an adjacent carbon atom such that during cleavage of the fragmentable bond the leaving group is disconnected from the adjacent carbon atom, e.g., via an intramolecular cyclization induced by an initial nucleophilic substitution of the oxygen of the peptidic amido linkage on the carbon in alpha position of the leaving group as depicted in FIG. 3. The stability of the fragmentable bonds of the crosslinking reagents is such that the bonds are capable of being selectively fragmented in a mass spectrometer system under ionization conditions that do not fragment the backbone of a peptide.

In certain embodiments, the fragmentable bonds of the subject crosslinking reagents connect a sulfonium, phosphonium or ammonium group to an adjacent carbon atom. In particular embodiments, the leaving group is a sulfonium leaving group (e.g., $-S^+(CH_3)R$). Disconnection of the sulphonium leaving group from the adjacent carbon atom (e.g., by fragmentation of the fragmentable bond during a nucleophilic substitution reaction at the adjacent carbon atom) results in neutral loss of a thioether group (e.g., $S(CH_3)R$). The chemical and biological applications of sulphonium, phosphonium and ammonium groups are known to those of skill in the art. See for example: Stirling and Patai, The Chemistry of the Sulfonium Group, Wiley: New York, 1981; Lundblad, Techniques in Protein Modification, Chapter 8 "The Modification of Methionine" CRC Press. Florida, 1995; Liu, "The role of Sulfur in Proteins" In: The Proteins, Volume III, Neurath, Hill and Boeder. Eds., Academic NY, 1977, Chapter 3, pp 239-402.

As noted above, the stability of the fragmentable bonds of the subject crosslinking reagents is such that the bonds are capable of being selectively fragmented in a mass spectrometer system under ionization conditions that do not fragment the backbone of a peptide. An exemplary cleavage reaction of the fragmentable bonds is shown in FIG. 3, that involves a nucleophilic substitution reaction of the carbonyl oxygen atoms with the carbon atoms that are adjacent to the sulphonium leaving groups, thereby breaking the covalent bonds adjacent to the sulphonium leaving groups to release a reporter product and two peptide-containing products that are each positively charged. In certain embodiments, the crosslinking reagent contains heterosubstituted carbonyl groups instead of carbonyl groups that are capable of undergoing a reaction of the same mechanism as shown in FIG. 3, and discussed above. The fragmentation reactions may be described as occurring via a cyclization-release mechanism where the peptide-containing products that are produced each contain a non-peptidic cyclic group. For fragmentation reactions involving the formation of such a cyclic group, the ring size and stability of the cyclic group being formed may determine in part the kinetics of the fragmentation reaction. In general, the formation of cyclic groups having a ring size of 4 to 7 (e.g., a ring size of 4, 5, 6 or 7) is desirable (e.g., more stable, less sterically strained rings) and results in desirable fragmentation reaction outcomes. Thus, in general the carbonyl or heterosubstituted carbonyl groups of the subject crosslinking reagents are separated from the carbon atom adjacent to the sulphonium, phosphonium or ammonium leaving group by a linker of 3, 4 or 5 atoms in length, such that the non-peptidic cyclic group of any peptide-containing products would have a ring size of 5, 6 or 7.

The peptide-containing products of the fragmentation reaction, in addition to containing a non-peptidic cyclic group, are also each positively charged (see e.g., the imidate groups of the peptide-containing products depicted in FIG. 3). In certain embodiments, the peptide-containing products of the fragmentation reaction contain non-peptidic cyclic groups (e.g., cyclic imidate groups that are remnants of the crosslinking reagent) that do not fragment under ionization conditions that fragment the backbone of peptides. Fragmentation of the non-peptidic component of the peptide-containing products complicates the analysis of the peptides, e.g., by complicating the MS/MS spectra and resulting in failures to determine the identity of the peptides by database searching algorithms. The subject crosslinking reagents may be designed to include one or more isotopically labeled atoms at particular locations in the molecule such that these isotopically labeled atoms would be incorporated into any peptide-containing products of a cleavage reaction as part of the remnants of the crosslinking reagent. Such isotopic signatures can be used in the analysis of the peptides by mass spectroscopy, e.g., used in a data-dependent acquisition parameter to select only those species that demonstrate the isotopic signature for MS/MS fragmentation.

The reporter product of a crosslinking reagent includes the region of the molecule located between the fragmentable bonds. As illustrated in the exemplary fragmentation reaction of FIG. 3, when both fragmentable bonds of the crosslinked peptides are broken a reporter product is released that contains the trifunctional scaffold and two neutral thioether moieties that are products of the two sulphonium leaving groups. The reporter product, upon release from the compound, has a characteristic mass to charge ratio. In some embodiments, the reporter product may further include an affinity tag. In other embodiments, the reporter product lacks the affinity tag but does include a remnant component of a cleavable linker that once connected the affinity tag to the trifunctional scaffold. Such a remnant component is produced when the cleavable linker $L^1$ is cleaved and released from the affinity tag that is bound to a solid support through its complementary affinity member.

Also provided are subject crosslinking reagents of various lengths that provide for a range of different maximum distances between the protein linking groups. In particular, the linkers and trifunctional scaffolds of the crosslinking reagents may be selected to provide for a backbone of up to 30 atoms in length, or a maximum distance of up to 50 angstroms, between the protein linking groups. In certain embodiments, the crosslinking reagent is described by formula (I), where the compound provides for a maximum distance between protein linking groups of 10 to 50 angstroms, such as, 10 to 40, 10 to 30, 10 to 25 or 10 to 20 angstroms. In certain embodiments, the crosslinking reagent is described by formula (I), where the protein linking groups are separated by a backbone of 9 to 30 atoms in length, such as 9 to 25, 9 to 20, 9 to 16, or 11 to 16 atoms in length. By designing the length of the arms of the crosslinking reagent, a particular distance between the two protein linking groups can be selected in the crosslinking reagent to provide for crosslinking reaction between accessible amino acid residues of protein complexes that are the same distance apart, i.e., 10 to 50 angstroms apart, such as, 10 to 40, 10 to 30, 10 to 25 or 10 to 20 angstroms.

An additional aspect of the subject crosslinking reagents is that one or more hydrophilic groups may readily be incorporated into the molecule, to improve the solubility of the reagents in an aqueous buffer. For example, one or more polyethyleneglycol linkers may be incorporated, sulfo-NHS active esters may be used instead of NHS esters as protein linking groups, and one or more hydrophilic substituents may be added to the trifunctional scaffold of the crosslinking reagent. In addition, since the subject crosslinking reagents can be built in a modular fashion, the lengths between the protein linking groups and the protein linking groups themselves, the cleavable linker and the affinity tag, may be varied all while maintaining water solubility of the reagents.

A further aspect of the subject crosslinking reagents is that if desired an isotopic signature can be incorporated at one or more of several possible locations in the molecule to confer on the resulting crosslinking reagent an isotopic signature useful in mass spectroscopic analysis. This isotopic signature can be incorporated through the use of halogens (1 or 2 bromine or chlorine atoms) or using heavy isotopes of carbon, hydrogen, nitrogen, oxygen, phosphorus and/or sulfur.

Crosslinking can be accomplished by any number of different ways depending on the design of the crosslinking reagent. By designing the length of the arms of the crosslinking reagent, a particular distance between the two protein linking groups can be selected to crosslink accessible amino acid residues of protein complexes. The protein linking groups may react to cross-link a first accessible amino acid sidechain group of a first protein with a second accessible amino acid sidechain group of a second protein where the proteins are within 10 Å to 50 Å (e.g., 15 Å to 30 Å) of each other. The distance between the protein linking groups may be selected as part of the crosslinking reagent design to selectively crosslink first and second amino acid sidechain residues of first and second proteins of a protein-protein complex. In particular embodiments, the maximum distance between protein linking groups in the subject crosslinking reagent is 10 to 50 angstroms, such as, 10 to 40, 10 to 30, 10 to 25 or 10 to 20 angstroms. In particular embodiments, the protein linking groups are separated by a backbone of 9 to 30 atoms in length, such as 9 to 25, 9 to 20, 9 to 16, or 11 to 16 atoms in length. If the maximum distance between protein linking groups is too large (e.g., greater than 50 angstroms) the crosslinking reagent may result in indiscriminant crosslinking of proteins not associated with each other in a protein complex.

A variety of protein linking groups are known to those of skill in the art and find use in the subject modified compounds. Any groups known to those of skill in the art may be used in the subject crosslinking reagents to cross-link proteins of interest, for example, groups as described in G. T. Hermanson, "Bioconjugate Techniques" Academic Press, 2nd Ed., 2008. Functional groups that may be used as protein linking groups include, but are not limited to, active esters, isocyanates, imidoesters, hydrazides, amino groups, aldehydes, ketones, photoreactive groups, maleimide groups, alpha-halo-acetyl groups, epoxides, azirdines, and the like.

In some cases, the crosslinking reagent is described by formula (I), where each protein linking group is independently selected from an amino-reactive group, a sulfhydryl reactive group, a hydroxyl reactive group, an imidazolyl reactive group and a guanidinyl reactive group. In particular embodiments, each protein linking group is independently selected from N-hydroxysuccinimidyl ester, sulfo-N-hydroxysuccinimidyl ester, a halo-substituted phenol ester, pentafluorophenol ester, a nitro-substituted phenol ester, an anhydride, isocyanate, isothiocyanate, an imidoester, maleimide, iodoacetyl, hydrazide, an aldehyde, an epoxide, an amino and a photoreactive linking group.

In some embodiments, the crosslinking reagent is described by formula (II):

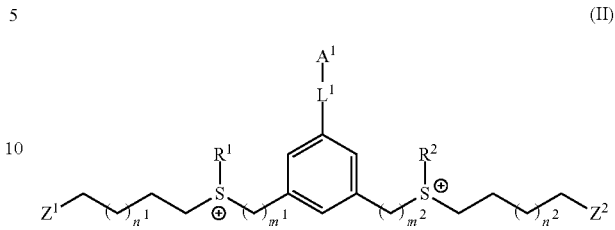

where $A^1$ is an affinity tag;
$L^1$ is a linker;
$R^1$ and $R^2$ are each independently an alkyl group;
$n^1$ and $n^2$ are independently 0, 1 or 2;
$m^1$ and $m^2$ are independently 0 or 1; and
$Z^1$ and $Z^2$ each independently include a protein linking group;
where $Z^1$ and $Z^2$ each include a carbonyl or a heterosubstituted carbonyl group in a position adjacent to the first methylene of the scaffold-linking arms to which $Z^1$ and $Z^2$ are attached, respectively; and
where the carbonyl or heterosubstituted carbonyl groups of $Z^1$ and $Z^2$ are each independently of the structure —C(=Y)—, wherein Y is O, S or $NR^3$ and where $R^3$ is selected from hydrogen and an alkyl.

In certain embodiments, the crosslinking reagent is described by formula (II), where $Z^1$ and $Z^2$ are each independently an active ester;
$n^1$, $n^2$, $m^1$ and $m^2$ are 1;
$R^1$ and $R^2$ are each independently a lower alkyl;
$L^1$ is a cleavable linker; and
$A^1$ includes a biotin moiety.

In particular embodiments, the crosslinking reagent is described by formula (II), where $Z^1$ and $Z^2$ are independently selected from —C(=Y)W and —C(=Y)NH-$T^3$-$Z^3$;
where Y is O, S or NH, W is a leaving group, $T^3$ is a linker and $Z^3$ is a protein linking group.

In certain cases, the crosslinking reagent is described by formula (II), where at least one of $Z^1$ and $Z^2$ is —C(=Y)NH-$T^3$-$Z^3$, where Y, $T^3$ and $Z^3$ are as defined above. In particular embodiments, $Z^3$ is selected from an iodoacetyl group, a maleimide, a photoreactive linking group, an aldehyde and an epoxide.

$Z^1$ and $Z^2$ are in certain cases described above as having both a protein linking group and a carbonyl or heterosubstituted carbonyl group. For clarity, this terminology is specifically used to describe: a) compounds in which moiety $Z^1$ and/or $Z^2$ contains a carbonyl or heterosubstituted carbonyl group that is part of the protein linking group, as well as b) compounds in which moiety $Z^1$ and/or $Z^2$ contains a carbonyl or heterosubstituted carbonyl group that is separate from the protein linking group. For example, where $Z^1$ or $Z^2$ is —C(=O)NH-$T^3$-$Z^3$ (where $T^3$ is a linker and $Z^3$ is a protein linking group), the carbonyl of the amido group (—C(=O)NH—) is separate from the protein linking group $Z^3$, which may be an active ester. Likewise, where $Z^1$ or $Z^2$ is an NHS ester (i.e., $Z^1$ or $Z^2$=—C(=O)—NHS), the carbonyl group of $Z^1$ or $Z^2$ is part of the protein linking group. As such, if a $Z^1$ or $Z^2$ group is referred to as having both a protein linking group and a carbonyl or heterosubstituted carbonyl group, then it is understood that both arrangements of groups are being described.

The subject crosslinking reagents may be prepared using by one or more methods, the chemistry and steps of which are known to one of ordinary skill in the art. One exemplary method is illustrated in Scheme 1 below, however there are many other routes that would lead to the same molecule. In the first step of the synthesis, the triphenylmethanethiol is deprotonated and reacted to nucleophilically displace the bromine atom of the bromovaleric acid. Next, the trityl protecting group is removed from the thiol, e.g., using the method described by Majer, et al. ("Synthesis and biological evaluation of thiol-based inhibitors of glutamate carboxypeptidase II: discovery of an orally active GCP II inhibitor," J. Med. Chem., 2003, 46 (10), p. 1989-96). Two equivalents of the free thiol are then used to react with the di-bromo trifunctional scaffold shown to construct the bis-thioether backbone. A carbodiimide coupling can be performed to install the protein linking NHS ester groups, and finally the sulfonium functionality can be made by reaction of the thioether groups with iodomethane, e.g., by the method described by Lu, et al. ("Ionic reagent for controlling the gas-phase fragmentation reactions of cross-linked peptides," Anal. Chem., 2008, 80 (23), p. 9279-87).

design of the crosslinking reagent. Proteins of interest may interact with each other to form protein-protein complexes (i.e., a heterodimer or homodimer complex) that may also include other proteins and/or cofactors as part of the complex (i.e., a multimeric complex). The subject crosslinking reagents may be used to cross-link two members of such complexes. The length of the crosslinking reagent may be selected such that the reagent can intermolecularly cross-link the proteins of interest via accessible sidechain amino acid residues. The subject crosslinking reagents may also be used to investigate both intermolecular and intramolecular crosslinking in proteins and complexes of interest.

Crosslinking proteins of interest may result in intermolecular crosslinks. In addition, crosslinking may also result in the formation of intramolecular crosslinks or dead-end crosslinks. An intramolecular crosslink occurs when both protein linking groups of the crosslinking reagent cross-link to accessible amino acid residues in the same protein. An intramolecular crosslinked product may be produced where Scheme 1: Preparation of a crosslinking reagent

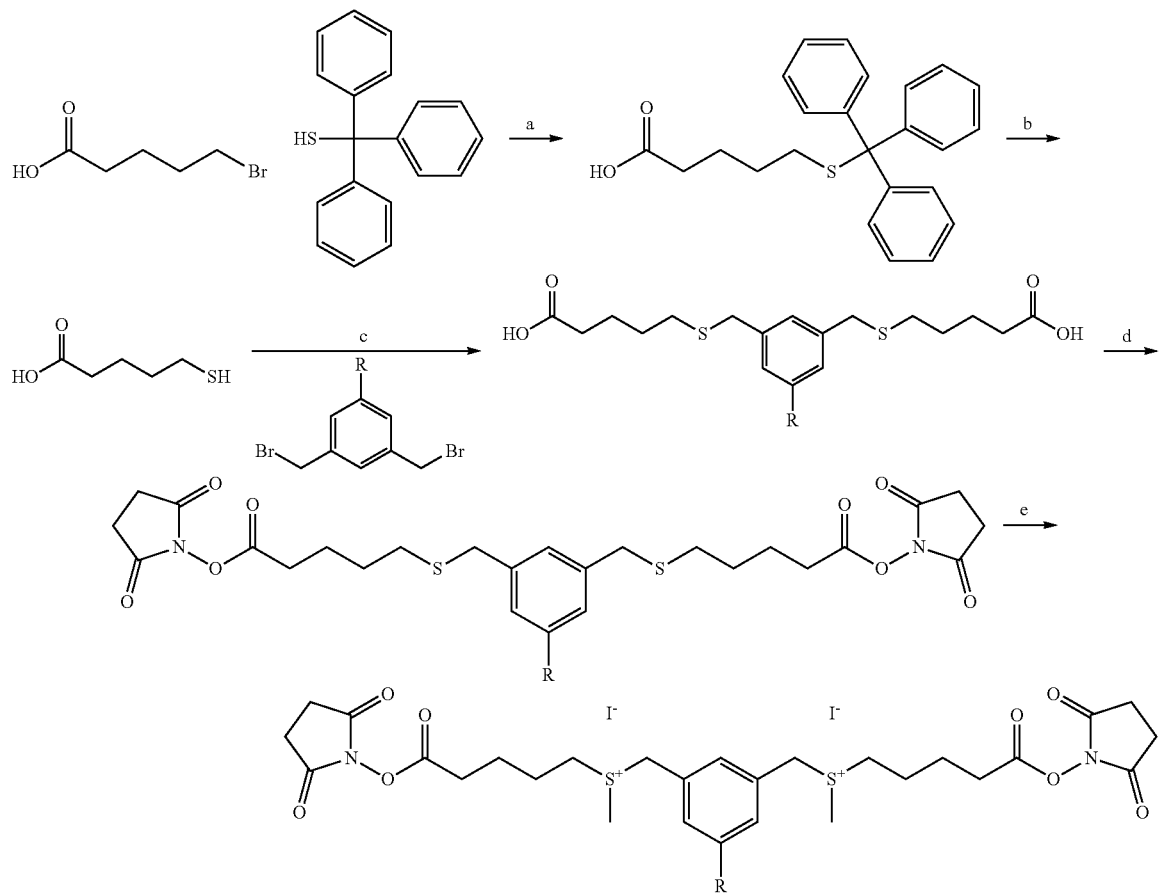

a) NaOMe, MeOH; b) TFA, (iPr)₃SiH, CH₂Cl₂; c) NaOMe, MeOH; d) NHS, DIC; e) CH₃I, CH₃CN

Crosslinked Polypeptides

Also provided are compounds of crosslinked polypeptides prepared using the subject crosslinking reagents and methods. The crosslinking of proteins of interest can be accomplished by any number of different ways depending on the two accessible amino acid residues that are crosslinked are contained within an amino acid sequence of the protein that does not contain a proteolytic site, i.e., digestion of the crosslinked product would produce a single crosslinked peptide product. A dead-end crosslink occurs when only one of the protein linking groups reacts with a sidechain residue and the other protein linking group is quenched, e.g., by hydrolysis in an aqueous solution. Such dead-end crosslinks may occur when the protein is not part of a protein-protein complex. In certain embodiments, the subject methods of analysis can be used to distinguish between an intermolecular crosslink, an intramolecular crosslink and a dead-end crosslink, using a variety of methods adapted from methods known to those of skill in the art.

In some embodiments, a subject compound including crosslinked polypeptides is described by formula (III):

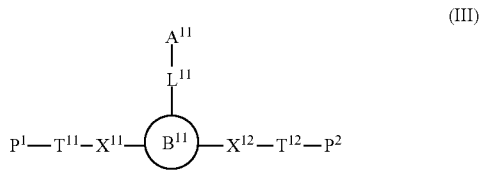

where $A^{11}$ is an affinity tag that may be present or absent;
$L^{11}$ is a linker;
$T^{11}$ and $T^{12}$ are each independently a linker of 3 to 6 atoms in length;
$B^{11}$ is a trifunctional scaffold;
$X^{11}$ and $X^{12}$ are independently selected from a sulfonium group, phosphonium group and an ammonium group; and
$P^1$ and $P^2$ each independently comprise a linked polypeptide and a carbonyl or a heterosubstituted carbonyl group in a position adjacent to $T^{11}$ and $T^{12}$ respectively.

The linked polypeptides may be proteins of interest, such as two proteins of a protein-protein complex. In other cases, the linked polypeptides may be digestion products of the proteins of interest, where the digestion has been performed using one or more proteases (e.g., trypsin).

In certain embodiments, the crosslinked polypeptides are described by formula (III), where the carbonyl or heterosubstituted carbonyl groups of $P^1$ and $P^2$ are each independently of the structure —C(=Y)—, where Y is O, S or $NR^3$ and where $R^3$ is selected from hydrogen and an alkyl; and the bond between $T^{11}$ and $X^{11}$ and the bond between $T^{12}$ and $X^{12}$ are each fragmentable in a mass spectrometer system under ionization conditions that do not fragment the backbone of a peptide. In particular embodiments, in formula (III), the —C(=Y)— group of $P^1$ is separated from $X^{11}$ by 3, 4, 5, 6 or 7 atoms and the —C(=Y)— group of $P^2$ is separated from $X^{12}$ by 3, 4, 5, 6 or 7 atoms.

In some cases, the subject compound including crosslinked polypeptides is characterized such that, under ionization conditions that do not fragment the backbone of a peptide, the —C(=Y)— groups of $P^1$ and $P^2$ react at sites adjacent to $X^{11}$ and $X^{12}$ to produce a reporter product and two peptide products.

Methods of Analysis

Provided herein are methods of characterization and analysis of protein-protein interactions. Also provided are methods of determining the identity of interacting proteins, including specific sites of interaction and the distance between these sites.

The subject crosslinking reagents and methods find use both in cell free samples (e.g., samples that include two or more isolated proteins, or a cell lysate or fraction of the same) and in samples that include intact cells (e.g., a tissue sample or cells grown in culture). In some embodiments, one or more proteins or complexes of interest may be isolated from a sample prior to characterization and analysis using the subject methods, e.g., using a binding moiety such as an antibody that specifically binds at least part of the protein or complex of interest. Such enrichment of proteins or complexes of interest in a sample may simplify the mass spectroscopic analysis of the peptide products. In some embodiments, the cell permeability of the crosslinking reagent is modulated such that the crosslinking reagent may target proteins of interest at specific sites within a cell. Crosslinking of proteins of interest may occur under conditions where the proteins are maintained in a folded state. The subject methods may include crosslinking of first and second proteins of a target protein-protein complex via accessible sidechain residues to produce a crosslinked polypeptide product. The crosslinking reaction can proceed via two steps. In the first step of this crosslinking reaction, one of the protein linking groups reacts with a first accessible amino acid sidechain of the first protein to produce an intermediate product. The remaining protein linking group that is attached to the intermediate product at the end of the crosslinking arm is capable of reacting with a second amino acid sidechain residue of a second protein that is accessible. Alternatively, the remaining protein linking group can react intramolecularly with a suitable second amino acid sidechain residue of the first protein. However, if the remaining protein linking group is quenched (e.g., via hydrolysis) before it can react intermolecularly with the second protein (or intramolecularly with the first protein), then a dead-end crosslink is produced. The length of the subject crosslinking reagents limits the crosslinking to only those proteins that are very proximal, such as the proteins in a protein-protein complex. In some cases, when the distance between the protein linking groups of the crosslinking reagent is too large (e.g., 50 Å or greater) the crosslinking reagent may not work, because the remaining protein linking group of the intermediate product could react indiscriminately with any number of non-complexed proteins.

In general terms, the method includes contacting a sample comprising a first polypeptide and a second polypeptide with a subject crosslinking reagent under conditions sufficient to cross-link the first protein and the second protein, to produce a first crosslinked product; digesting the first crosslinked product to produce a second crosslinked product; breaking the fragmentable bonds of the second crosslinked product under ionization conditions that do not fragment the backbone of a peptide, thereby producing: a) a reporter product, b) a first fragmentation product comprising a first peptide and c) a second fragmented product comprising a second peptide. The first and second fragmented products may then be analyzed in a mass spectrometer to identify the first and second peptides.

The digestion of polypeptides of interest using one or more proteases allows the polypeptides to be fragmented into smaller peptides suitable for sequence analysis (e.g., by Edman degradation or by mass spectroscopy). Trypsin may be employed in this step, although other enzymes could be used. Trypsin is an enzyme well suited for use in proteomics experiments for mass spectrometry analysis, e.g., in-gel digestion, since it has a very well defined specificity and produces peptide fragments containing either a C-terminal Arg or Lys residue. A variety of digestion methods and proteases for use in such methods are known to those of skill in the art and find use in the subject methods of analysis. The principle of peptide analysis, including protease digestion and sequencing of proteins by mass spectroscopic analysis are well known to those of skill in the art, see e.g., Domon, et al. "Mass Spectrometry and Protein Analysis," Science 312, 212 (2006).

A variety of protein crosslinking technologies are known to those of skill in the art and can be utilized in the subject crosslinking reagents and methods of analysis, see e.g., Leitner et al., "Probing native protein structures by chemical cross-linking, mass spectrometry and bioinformatics," Molecular & Cellular Proteomics, 9, 1634-1649, 2010.

In some embodiments of the subject method, the crosslinking reagent is described by formula (I), where $A^1$, $L^1$, $T^1$, $T^2$, $B^1$, $X^1$, $X^2$, $Z^1$ and $Z^2$ are as defined above, and where $Z^1$ and $Z^2$ each include a carbonyl or a heterosubstituted carbonyl group in a position adjacent to $T^1$ and $T^2$ respectively.

In certain embodiments of the subject method, breaking the fragmentable bonds includes reacting the carbonyl or heterosubstituted carbonyl groups at sites adjacent to $X^1$ and $X^2$ such that the fragmentable bonds of the crosslinked product are broken, where the first and second fragmentation products each comprise a cyclic group having a ring size of 5, 6 or 7 and comprising $T^1$ or $T^2$.

In some cases, the first polypeptide is suspected of interacting with the second polypeptide under native conditions (i.e., conditions where the polypeptide is maintained in a folded state) and the method further includes evaluating whether the first polypeptide specifically interacts with the second polypeptide.

The subject methods may further include, prior to the fragmenting step, isolating the second crosslinked product by affinity chromatography or magnetic beads. The second crosslinked product may be bound to an affinity support via its affinity tag to allow washing away of untagged polypeptide products of the digestion. The second crosslinked product may then be unbound from the affinity support either by competitive elution of the affinity tag or by cleavage of the cleavable linker connecting the affinity tag to the trifunctional scaffold.

In certain embodiments, the subject method includes the use of a crosslinking reagent described by formula (I) above, where $L^1$ is a cleavable linker, and the subject method further includes: 1) cleaving $L^1$ to release the second crosslinked product from the affinity support; and 2) eluting the crosslinked product from the affinity support.

After the crosslinked product has been isolated by affinity chromatography, the fragmentable bonds of the product may be fragmented and the resulting peptide products analyzed. The fragmentation of the fragmentable bonds can happen at any point in the analysis. For example, the fragmentable bonds can be fragmented anywhere in a mass spectrometer during analysis, such as, in-source (i.e. at the ion source), during transport of the ions, or in a collision cell.

Analysis of the subject crosslinked peptides by mass spectroscopy is simplified when these fragmentable bonds are fragmented without fragmentation of the backbones of the peptides, because fragmentation of the crosslinked peptides releases two peptide products in conjunction with a characteristic reporter product that identifies the presence of the peptide products. The reporter product has a detectable property (e.g., a particular mass to charge ratio, m/z) that is independent of the peptidic content of the crosslinked peptides. The reporter product serves to identify fractions that have crosslinked peptides, even where such fractions are present as a small percentage of a large, complex mixture of proteins and cross-linkers. Following the release of the reporter product, the peptide products of fragmentation may be selected for further sequence analysis (e.g., by tandem mass spectroscopy) to determine the identity of parent proteins that were crosslinked. In addition, the peptide products of fragmentation each include a non-peptidic cyclic group (e.g., a cyclic imidate) that contains a positive charge thus facilitating analysis of the peptides, e.g., by electrospray mass spectroscopy.

Analysis of the first and second peptides may be performed by mass spectrometry, e.g., tandem mass spectrometry. The mass spectrometer may be equipped with electrospray ionization (ESI) or matrix assisted laser desorption ionization (MALDI) interfaces to transfer the protein or peptide ion from solution into the gas-phase. Mass analysers that are applicable to tandem mass spectrometry fall into two basic categories: tandem-in-space and tandem-in-time. Combinations of these types also can be used. Tandem-in-space mass spectrometers have discreet mass analysers for each stage of mass spectrometry; examples include sector (commonly double focusing sector and "hybrid" combinations of sector and quadrupole analyser instruments), time of flight and triple quadrupole instruments, as well as "hybrid" combinations of time of flight and quadrupole instruments. Tandem-in-time mass instruments have only one mass analyser, and each stage of mass spectrometry takes place in the same region, but is separated in time via a sequence of events. Examples of tandem in time mass analysers include both two- and three-dimensional quadrupole ion trap and Fourier-transform ion cyclotron resonance (FT-ICR) mass spectrometers.

The subject methods can be used to compare two samples to detect changes in one sample relative to another. For example, the subject methods may be used to analyse two samples where one of the samples is the cell lysate of a cell culture that was subjected to a change in environment or a particular test condition (e.g., addition of a compound), and the other of the samples is a reference sample. Such data can be used to identity protein-protein interactions and map a proteomic network.

Kits

Also provided by the present disclosure are kits for practicing the above described subject method. The subject kits contain at least the crosslinking reagent. The kit may also contain reagents for cross-linking, affinity purification, etc., and may also contain positive and/or negative controls to be run in conjunction with an assay. The various components of the kit may be present in separate containers or certain compatible components may be pre-combined into a single container, as desired.

In addition to above-mentioned components, the subject kits may further include instructions for using the components of the kit to practice the subject methods, i.e., instructions for sample analysis. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g., CD-ROM, diskette, etc. In yet other embodiments, the actual instructions are not present in the kit, but means for obtaining the instructions from a remote source, e.g., via the internet, are provided. An example of this embodiment is a kit that includes a web address where the instructions can be viewed and/or from which the instructions can be downloaded.

Although the particular embodiments have been described in some detail by way of illustration and example for purposes of clarity of understanding, it is readily apparent in light of the teachings of this invention that certain changes and modifications may be made thereto without departing from the spirit or scope of the appended claims. Accordingly, the preceding merely illustrates the principles of the invention. Various arrangements may be devised which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A compound of the structure:

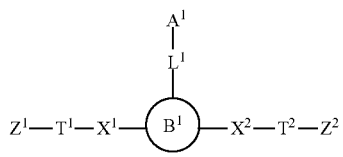

wherein $A^1$ is an affinity tag;
$L^1$ is a linker;
$T^1$ and $T^2$ are each independently a linker of 3 to 6 atoms in length;
$B^1$ is a trifunctional scaffold;
$X^1$ and $X^2$ are independently selected from a sulfonium group, a phosphonium group and an ammonium group; and
$Z^1$ and $Z^2$ each independently comprise a protein linking group;
wherein $Z^1$ and $Z^2$ each comprise a carbonyl or a heterosubstituted carbonyl group in a position adjacent to $T^1$ and $T^2$ respectively.

2. The compound of claim 1, wherein the bond between $T^1$ and $X^1$ and the bond between $T^2$ and $X^2$ are each fragmentable in a mass spectrometer system under ionization conditions that do not fragment the backbone of a peptide.

3. The compound of claim 1, wherein the compound provides for a maximum distance between protein linking groups of about 10 to about 30 angstroms.

4. The compound of claim 1, wherein the protein linking groups are separated by a backbone of 9 to 30 atoms in length.

5. The compound of claim 1, wherein:
each protein linking group is independently selected from an amino-reactive group, a sulfhydryl reactive group, a hydroxyl reactive group, an imidazolyl reactive group and a guanidinyl reactive group.

6. The compound of claim 1, wherein:
each protein linking group is independently selected from N-hydroxysuccinimidyl ester, sulfo-N-hydroxysuccinimidyl ester, a halo-substituted phenol ester, pentafluorophenol ester, a nitro-substituted phenol ester, an anhydride, isocyanate, isothiocyanate, an imidoester, maleimide, iodoacetyl, hydrazide, an aldehyde, an epoxide, an amino and a photoreactive linking group.

7. The compound of claim 1, wherein the compound is of the structure:

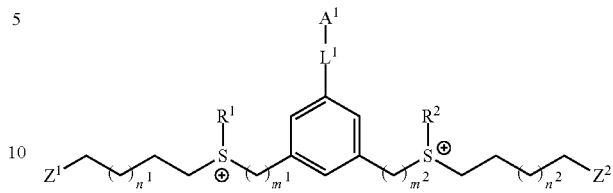

wherein $R^1$ and $R^2$ are each independently an alkyl group;
$n^1$ and $n^2$ are independently 0, 1 or 2; and
$m^1$ and $m^2$ are independently 0 or 1;
wherein the carbonyl or heterosubstituted carbonyl groups of $Z^1$ and $Z^2$ are each independently of the structure —C(=Y)—, wherein Y is O, S or $NR^3$ and wherein $R^3$ is selected from hydrogen and an alkyl.

8. The compound of claim 7, wherein:
$Z^1$ and $Z^2$ are each independently an active ester;
$n^1$, $n^2$, $m^1$ and $m^2$ are 1;
$R^1$ and $R^2$ are each independently a lower alkyl;
$L^1$ is a cleavable linker; and
$A^1$ comprises a biotin moiety.

9. The compound of claim 7, wherein:
$Z^1$ and $Z^2$ are independently selected from —C(=Y)W and —C(=Y)NH-$T^3$-$Z^3$;
wherein Y is O, S or NH;
W is a leaving group;
$T^3$ is a linker; and
$Z^3$ is a protein linking group.

10. The compound of claim 9, wherein at least one of $Z^1$ and $Z^2$ is —C(=Y)NH-$T^3$-$Z^3$ wherein $Z^3$ is selected from an iodoacetyl group, a maleimide, a photoreactive linking group, an aldehyde and an epoxide.

11. A compound comprising crosslinked polypeptides, wherein the compound is of the structure:

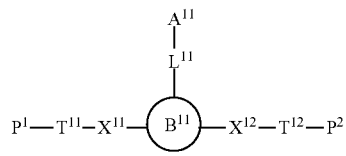

wherein $A^{11}$ is an affinity tag;
$L^{11}$ is a linker;
$T^{11}$ and $T^{12}$ are each independently a linker of 3 to 6 atoms in length;
$B^{11}$ is a trifunctional scaffold;
$X^{11}$ and $X^{12}$ are independently selected from a sulfonium group, phosphonium group and an ammonium; and
$P^1$ and $P^2$ each independently comprise a linked polypeptide and a carbonyl or a heterosubstituted carbonyl group in a position adjacent to $T^{11}$ and $T^{12}$ respectively.

12. The compound of claim 11, wherein:
wherein the carbonyl or heterosubstituted carbonyl groups of $P^1$ and $P^2$ are each independently of the structure —C(=Y)—, wherein Y is O, S or $NR^3$ and wherein $R^3$ is selected from hydrogen and an alkyl; and
the bond between $T^{11}$ and $X^{11}$ and the bond between $T^{12}$ and $X^{12}$ are each fragmentable in a mass spectrometer system under ionization conditions that do not fragment the backbone of a peptide.

13. The compound of claim 12, wherein:
the —C(=Y)— group of $P^1$ is separated from $X^{11}$ by 3 to 6 atoms and the —C(=Y)— group of $P^2$ is separated from $X^{12}$ by 3 to 6 atoms;
wherein the compound is characterized such that, under ionization conditions that do not fragment the backbone of a peptide, the —C(=Y)— groups of $P^1$ and $P^2$ react at sites adjacent to $X^{11}$ and $X^{12}$ to produce a reporter product and two polypeptide products.

14. A kit for analyzing a non-covalently associated complex of polypeptides, the kit comprising the compound of claim 1, and instructions for use of the compound.

* * * * *